United States Patent [19]

Shoesmith, deceased

[11] Patent Number: Plant 6,157

[45] Date of Patent: Apr. 19, 1988

[54] CHRYSANTHEMUM PLANT NAMED PIROUETTE

[75] Inventor: Leonard H. Shoesmith, deceased, late of Woking, England, by May Victoria Shoesmith, executrix

[73] Assignee: Ball PanAm Plant Company, Parrish, Fla.

[21] Appl. No.: 872,909

[22] Filed: Jun. 11, 1986

[51] Int. Cl.[4] ..... A01H 5/00

[52] U.S. Cl. ..... Plt./76

[58] Field of Search ..... Plt./76

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Pirouette having flat capitulum form and decorative capitulum type, quilled decorative flower type, pale lavender pink flower color, nine week flowering response, strong stems, 15–25 cm. peduncles, adaptation to cultivation as a cut spray in year around programs, and ability to ship and keep well.

1 Drawing Sheet

The present invention comprises a new and distinct cultivar of *Chrysanthemum morifolium,* Ramat., hereinafter referred to by the cultivar name Pirouette.

Pirouette was originated from a hybridization made in a controlled breeding program in Westfield, Woking, England in 1978. The male and female parents are unknown at this time.

Pirouette was discovered and selected as one flowering plant within the progeny of the stated parentage by Leonard H. Shoesmith in November of 1979 in a controlled environment in West Chicago, Ill., and was given the code #SP-79-1590-PS.

The first act of asexual reproduction of Pirouette was accomplished when vegetative cuttings were taken from the initial selection in February of 1980 in a controlled environment in West Chicago, Ill. by a technician working under formulations established and supervised by applicant. Horticultural examination of selected units initiated in May of 1979 has demonstrated that the combination of characteristics as herein disclosed for Pirouette are firmly fixed and are retained through successive generations of asexual reproduction.

Pirouette has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Pirouette, which in combination distinguish this Chrysanthemum as a new and distinct cultivar.

(1) A distinctive novelty type plant adapted for cultivation as a cut spray in year around programs.

(2) Nine week flowering response.

(3) Quilled decorative flower type.

(4) Pale lavender pink flower color (color fades to almost white if night temperatures are above 85°).

(5) Strong stems.

(6) 15–25 cm. peduncles.

(7) Ability to ship and keep well.

The accompanying photographic drawing shows typical inflorescence and foliage characteristics of Pirouette, with colors being as nearly true as possible with illustrations of this type.

Sheet 1 is a black and white photograph with the true floret color appearing in one flower.

In the following description, color references are made to The Royal Horticultural Society Colour Chart. The color values were determined between 12:00 Noon and 1:00 p.m. on May 21, 1986 under natural light conditions at Bradenton, Fla.

Classification:

*Botanical.*—*Chrysanthemum morifolium,* Ramat., cv Pirouette.

*Commercial.*—Pompon or cut spray.

INFLORESCENCE

A. Capitulum:

*Form.*—Flat.

*Type.*—Decorative to loose spider.

*Diameter across face.*—8–12 cm.

B. Corolla of ray florets:

*Color (general tonality from a distance of three meters).*—Pale pink.

*Color (upper surface).*—75C-D.

*Color (under surface).*—65C.

C. Corolla of disc florets: None present.

D. Reproductive organs:

*Androecium.*—Insignificant.

*Gynoecium.*—Insignificant.

PLANT

A. General appearance:

*Height.*—At finish, 1–2 meters.

B. Foliage:

*Color (upper surface).*—147A.

*Color (under surface).*—147B.

*Shape.*—Deeply lobed and slightly serrated.

I claim:

1. A new and distinct cultivar of Chrysanthemum plant named Pirouette, as illustrated and described, and particularly characterized by its quilled decorative flower type, pale lavender pink flower color, nine week flowering response, strong stems, 15–25 cm. peduncles, its adaptation to cultivation as a cut spray in year around programs, and by its ability to ship and keep well.

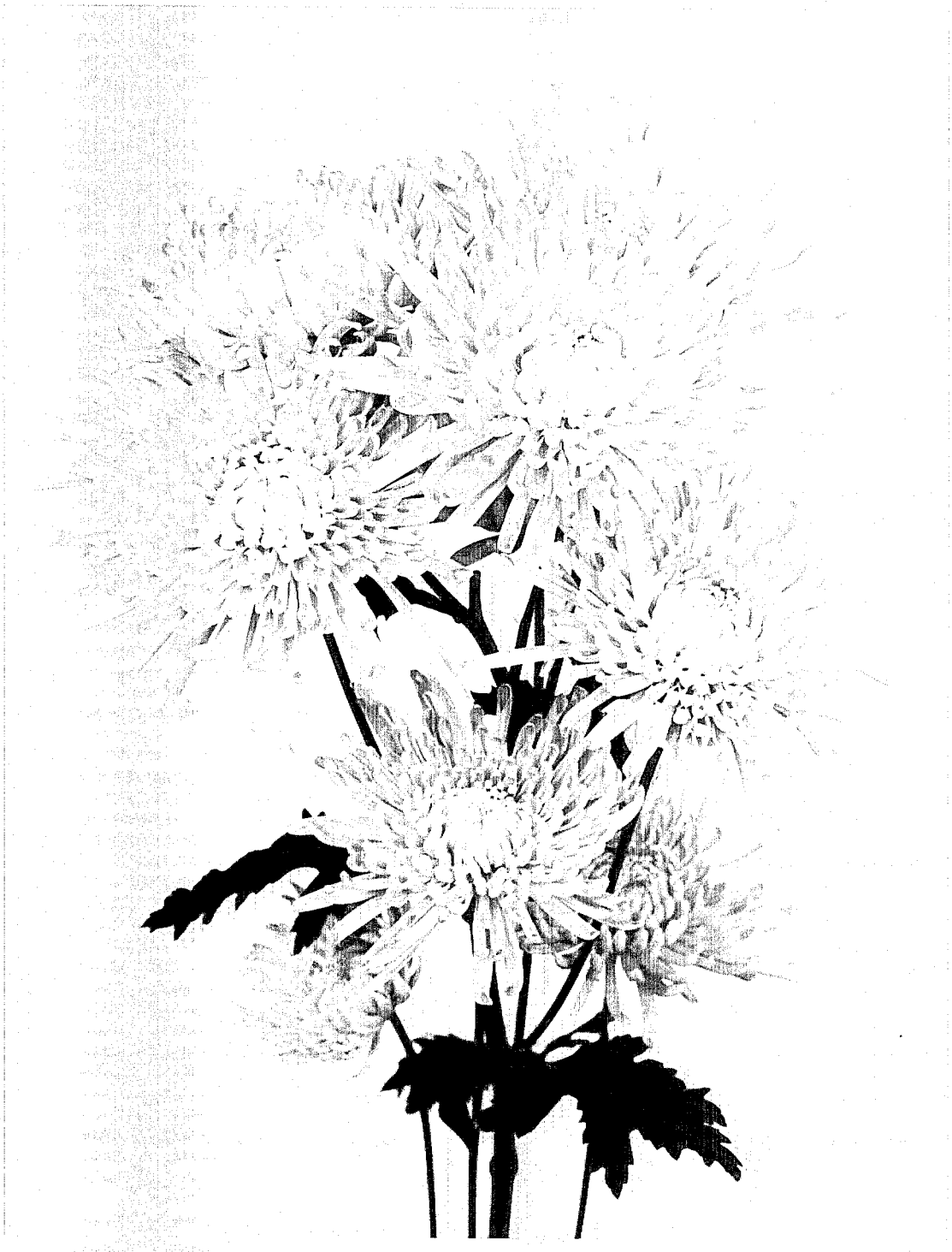

* * * * *